United States Patent
Kinuta et al.

(10) Patent No.: US 10,641,689 B2
(45) Date of Patent: May 5, 2020

(54) METHOD OF PREPARING GLASS SLIDE SPECIMEN OF CELLS

(71) Applicant: OPTNICS PRECISION CO., LTD., Ashikaga-shi, Tochigi (JP)

(72) Inventors: Seichin Kinuta, Tochigi (JP); Yoshiyuki Ichinosawa, Tochigi (JP); Hayao Nakanishi, Aichi (JP); Seiji Ito, Aichi (JP)

(73) Assignee: OPTNICS PRECISION CO., LTD., Ashikaga-shi, Tochigi (JP)

( * ) Notice: Subject to any disclaimer, the term of this patent is extended or adjusted under 35 U.S.C. 154(b) by 73 days.

(21) Appl. No.: 15/739,788

(22) PCT Filed: Jun. 16, 2017

(86) PCT No.: PCT/JP2017/022345
§ 371 (c)(1),
(2) Date: Dec. 26, 2017

(87) PCT Pub. No.: WO2018/020897
PCT Pub. Date: Feb. 1, 2018

(65) Prior Publication Data
US 2019/0120735 A1 Apr. 25, 2019

(30) Foreign Application Priority Data
Jul. 25, 2016 (JP) ................................. 2016-145568

(51) Int. Cl.
| | | |
|---|---|---|
| G01N 1/31 | (2006.01) | |
| G02B 21/34 | (2006.01) | |
| C12M 1/34 | (2006.01) | |
| C12M 1/00 | (2006.01) | |
| C12M 1/26 | (2006.01) | |
| G01N 1/28 | (2006.01) | |
| C12N 15/10 | (2006.01) | |
| G01N 1/40 | (2006.01) | |

(52) U.S. Cl.
CPC .............. *G01N 1/312* (2013.01); *C12M 1/00* (2013.01); *C12M 1/26* (2013.01); *C12M 1/34* (2013.01); *C12N 15/1003* (2013.01); *G01N 1/28* (2013.01); *G01N 1/2813* (2013.01); *G01N 1/4077* (2013.01); *G02B 21/34* (2013.01); *G01N 2001/4088* (2013.01)

(58) Field of Classification Search
CPC .... G01N 1/312; C12N 15/1003; C12M 1/123
See application file for complete search history.

(56) References Cited

U.S. PATENT DOCUMENTS

| | | | |
|---|---|---|---|
| 5,143,627 A | 9/1992 | Lapidus et al. | |
| 2009/0286305 A1* | 11/2009 | Chu | B01D 11/02 435/270 |
| 2010/0248207 A1 | 9/2010 | Raz et al. | |
| 2012/0129164 A1* | 5/2012 | Cayre | C12M 33/04 435/6.1 |
| 2013/0095473 A1 | 4/2013 | Groelz | |
| 2013/0316347 A1* | 11/2013 | Brechot | G01N 33/5091 435/6.11 |
| 2013/0330721 A1* | 12/2013 | Tang | B01D 29/00 435/6.11 |
| 2015/0364307 A1* | 12/2015 | Agar | H01J 49/0418 356/72 |
| 2016/0136552 A1 | 5/2016 | Nakanishi et al. | |
| 2017/0268967 A1* | 9/2017 | Shao | B01D 63/081 |

FOREIGN PATENT DOCUMENTS

| | | |
|---|---|---|
| JP | H04-232834 A | 8/1992 |
| JP | H06-221976 A | 8/1994 |
| JP | 2010-530234 A | 9/2010 |
| JP | 2013-531987 A | 8/2013 |
| JP | 2014-200201 A | 10/2014 |
| KR | 20150035571 A | 4/2015 |
| WO | 2015/012315 A1 | 1/2015 |

OTHER PUBLICATIONS

Yusa A. et al, "Development of a New Rapid Isolation Device for Circulating Tumor Cells(CTCs) Using 3D Palladium Filter and Its Application for Genetic Analysis", PLOS One, 2014, vol. 9 Issue 2, e88821.
Office Action dated May 20 2019, issued by the KIPO in corresponding Korean Patent Application No. 10-2017-7037235.

* cited by examiner

*Primary Examiner* — Narayan K Bhat
(74) *Attorney, Agent, or Firm* — Solaris Intellectual Property Group, PLLC

(57) ABSTRACT

A device for preparing a glass slide specimen of cells has: a filter that has recesses, which capture target cells that are at least one of circulating tumor cells within blood or rare tumor cells within a body fluid, and pores that are formed in the recesses and that pass non-target cells therethrough; a glass slide that is superposed onto a surface of the filter, at a side at which the target cells are captured, and onto which the target cells are transferred; a cover member that is placed on a surface of the filter at a side opposite from the glass slide, and that seals in a buffer solution for immersing the target cells at interiors of the recesses; and a container into which the glass slide is immersed and in which is stored a preservation liquid that preserves the target cells that have been transferred onto the glass slide.

4 Claims, 14 Drawing Sheets

METHOD OF PREPARING GLASS SLIDE SPECIMEN OF CELLS

TECHNICAL FIELD

The present disclosure relates to a method of preparing a glass slide specimen of cells for target cells (circulating tumor cells within blood or rare tumor cells with a body fluid).

BACKGROUND ART

Many devices have been reported as devices that carry out the separation and detection of circulating tumor cells (hereinafter also called "CTCs") within blood, but CellSearch® from Veridex is the only one that has been approved by the Food and Drug Administration (FDA) of the United States and that is commercially available.

Further, Japanese Patent Application Laid-Open (JP-A) No. H06-221976 and U.S. Pat. No. 5,143,627 disclose devices and methods that, at the time of processing a general cytology sample of sputum or the like, easily and efficiently transfer general cells onto a glass slide by using a filter, and prepare a glass slide specimen. However, devices and methods that prepare glass slide specimens of CTCs have not been disclosed until now.

SUMMARY OF INVENTION

Technical Problem

Conventional CTC separating and detecting devices and methods such as the aforementioned CellSearch and the like carry out, in a dark field, determination of CTCs by combinations of marker expressions (keratin+/EpCAM+/CD45−) by fluorescent staining. Therefore, cytomorphological evaluation of CTCs such as nuclear chromatin patterns and the like is insufficient, and the evaluation of CTCs as cytodiagnosis is impossible. For this reason, in our country, CTC detection methods are not regarded to be cytologic examinations, and accordingly, are not covered by insurance. As CTC detecting methods, conventional fluorescence detecting methods are carried out as outsourced examinations for clinical testing by only a few examination companies, but the widespread use of such methods to general hospitals has not been achieved at all.

Further, in the sample processing methods and devices that are disclosed in aforementioned JP-A No. H06-221976 and U.S. Pat. No. 5,143,627, flat, general filters are used, and therefore, these methods and devices are effective in cases in which a large number of tumor cells exist within the sample of sputum or the like. However, in the case of an extremely rare cell sample in which usually only about a few CTCs or the like exist within 1 cc of blood, the cells are crushed or dry out, and cell damage arises. As a result, the efficiency of transfer onto a glass slide deteriorates, and, therefore, preparation of a glass slide sample is impossible.

On the other hand, in U.S. Pat. No. 5,961,889, the present applicant presents a metal filter that, via recesses that capture peripheral circulating tumor cells within blood or rare tumor cells, and pores that are formed in the bottom portions of the recesses, filters only the blood cells, and can concentrate the peripheral circulating tumor cells or rare tumor cells that are within a body fluid.

An object of the present disclosure is to, by applying the filter presented in aforementioned U.S. Pat. No. 5,961,889 as a device and method for preparing a glass slide specimen of cells, easily, rapidly and highly efficiently separate target cells that are circulating tumor cells within blood and/or rare tumor cells within a body fluid, and prepare a glass slide specimen at which the target cells have been transferred efficiently while keeping cell damage to the minimum, and thereby can be utilized in cytologic diagnosis and genetic testing and the like that include immunostaining, in a clinical laboratory of a general hospital.

Solution to Problem

The present disclosure includes the following features.

[1] A device for preparing a glass slide specimen of cells, comprising: a filter that has recesses, which capture target cells that are at least one of circulating tumor cells within blood or rare tumor cells within a body fluid, and pores that are formed in the recesses and that pass non-target cells therethrough; a glass slide that is superposed onto a surface of the filter, at a side at which the target cells are captured, and onto which the target cells are transferred; a cover member that is placed on a surface of the filter at a side opposite from the glass slide, and that seals in a buffer solution for immersing the target cells at interiors of the recesses; and a container into which the glass slide is immersed and in which is stored a preservation liquid that preserves the target cells that have been transferred onto the glass slide.

[2] A method of preparing a glass slide specimen of cells that has a filter that has recesses, which capture target cells that are at least one of circulating tumor cells within blood or rare tumor cells within a body fluid, and pores that are formed in the recesses and that pass non-target cells therethrough, the method comprising: a first step of separating, via the filter, the target cells from the non-target cells and capturing the target cells; a second step of superposing the filter on the glass slide such that a surface of the filter, at a side at which the target cells are captured, faces the glass slide, placing a cover member on the filter, and immersing the target cells, which are between the filter and the glass slide, in a buffer solution; a third step of transferring the target cells, which are between the filter and the glass slide, onto the glass slide under application of centrifugal force or under pressurization by air pressure; and a fourth step of, by immersing the glass slide in a container in which a preservation liquid is stored, causing the cover member and the filter to peel-off naturally from the slide glass and preserving the target cells without impairing the target cells.

[3] A method of preparing a glass slide specimen of cells that has a filter that has recesses, which capture target cells that are at least one of circulating tumor cells within blood or rare tumor cells within a body fluid, and pores that are formed in the recesses and that pass non-target cells therethrough, the method comprising: a first step of separating, via the filter, the target cells from the non-target cells and capturing the target cells; a second step of placing the target cells, which have been captured by the filter, in a buffer solution; a third step of causing the target cells that are within the buffer solution to cling to the glass slide, and adhering and transferring the target cells onto the glass slide while still living; and a fourth step of immersing the glass slide in a container in which a preservation liquid is stored, and preserving the target cells that have been transferred onto the glass slide.

[4] A method of extracting DNA or RNA comprising placing a tubular body onto a glass slide specimen of cells that has been obtained by the device for preparing a glass slide specimen of cells or the method of preparing a glass slide specimen of cells of any of [1] through [3], and, by the tubular body, surrounding a periphery of the target cells which have been transferred onto the glass slide, maintaining a DNA or RNA extraction liquid within the tubular body for a predetermined time, and extracting DNA or RNA from the target cells.

In accordance with the device for preparing a glass slide specimen of cells relating to [1] or the method of preparing a glass slide specimen of cells relating to [2], by using the filter (that is made of metal or is made of resin for example) that has the recesses, target cells (circulating tumor cells within blood and/or rare tumor cells within a body fluid) are separated without omission by using the difference in size between the target cells and non-target cells (e.g., blood cells), and the target cells can be captured in the recesses.

Further, because the target cells are immersed in the buffer solution that collects in the recesses of the filter, at the time when the target cells are transferred onto the glass slide, it is difficult for the target cells to be crushed or to dry-out, and cell damage is kept to a minimum, and the cell shape can be preserved well. Further, by immersing the glass slide in a container in which a preservation liquid is stored, and causing the cover member and the filter to peel-off naturally without applying superfluous external force, a glass slide specimen, in which the target cells are transferred onto a glass slide without being dried-out and in a state in which their forms are preserved well, is obtained.

In accordance with the method of preparing a glass slide specimen of cells relating to [3], by using the difference in size between target cells (circulating tumor cells within blood or rare tumor cells within a body fluid) and non-target cells (e.g., blood cells), the target cells can be separated and captured conveniently, rapidly and highly-efficiently by the filter (that is made of metal or is made of resin for example) that has the recesses. By placing the captured target cells into a buffer solution and causing them to cling to a glass slide, and adhering and transferring the target cells onto the glass slide while still living, these target cells can be transferred onto the glass slide while cell damage is kept to a minimum.

In accordance with the method of preparing a glass slide specimen of cells relating to [4], after target cells are fixed on the filter, these target cells can be easily and efficiently recovered and transferred from the filter onto a glass slide. By using the glass slide specimen of the target cells, for example, Papanicolau staining or immunostaining can be carried out as routine work of a laboratory, and moreover, DNA or RNA is easily extracted from this glass slide specimen, and genetic analysis can be carried out. In this way, the Papanicolau staining or immunostaining using the glass slide specimen is a permanent specimen. Therefore, as compared with a judgment by fluorescent staining, not only measurement of the number of cells and more objective evaluation in a light visual field by plural cytologists or pathologists are possible, but also, easy and inexpensive utilization as a liquid biopsy such as cytologic diagnosis or genetic analysis or the like of the target cells is possible.

Advantageous Effects of Invention

In accordance with the present disclosure, target cells that are circulating tumor cells and/or rare tumor cells are easily, rapidly and highly efficiently separated by a filter having recesses, and are transferred efficiently onto a glass slide while keeping cell damage to the minimum, and can be utilized in cytologic diagnosis and genetic testing and the like that include immunostaining, in a clinical laboratory of a general hospital.

BRIEF DESCRIPTION OF DRAWINGS

FIG. 1 through FIG. 16 relate to a first embodiment, and FIG. 1 is a cross-sectional view showing a state in which a body fluid that contains cells is flowing in a filter unit having a filter.

FIG. 2 is a cross-sectional view showing a state in which target cells are captured by the filter.

FIG. 5 is an enlarged sectional view showing a state in which the filter is superposed on a glass slide.

FIG. 6 is an enlarged sectional view showing a state in which a buffer solution is injected between a cover member and the glass slide.

FIG. 7 is an enlarged sectional view showing a state in which the target cells are immersed in the buffer solution.

FIG. 8 is an enlarged sectional view showing a state in which the glass slide, the 3D metal filter and the cover member are superposed, and target cells that are positioned between the 3D metal filter and the glass slide are immersed in the buffer solution.

FIG. 9 is an enlarged sectional view showing a state in which the glass slide, the 3D resin filter and the cover member are superposed, and the target cells are positioned between the 3D resin filter and the glass slide.

FIG. 10 is a side view showing a state in which the target cells are transferred onto the glass slide by a centrifuge.

FIG. 11 is a graph showing the relationship between the rotational speed of the centrifuge and the recovery rate of cells.

FIG. 12 is a cross-sectional view showing that the target cells captured on the filter are placed in a buffer solution, the filter is set tightly on the glass slide whose surface has been coated by a substance that promotes adhesion, and pressurization by air pressure or the like from above is carried out by using a syringe-type pressurizing instrument, and, due thereto, the target cells can be transferred onto the glass slide in a stamped manner.

FIG. 13 is a cross-sectional view showing a state in which the glass slide onto which the target cells have been transferred is immersed in a preservation liquid, and the cover member and the filter are peeled-off from the glass slide by naturally falling-down due to gravity.

FIG. 14 is a cross-sectional view showing a glass slide specimen.

FIG. 15 is a microscope photograph showing Papanicolau staining of the glass slide specimen. The nuclear chromatin pattern and the cytoplasm of tumor cells are observed clearly.

FIG. 16 is microscope photographs of cells that have been subjected to various types of immunostaining.

DESCRIPTION OF EMBODIMENTS

Figure 1:
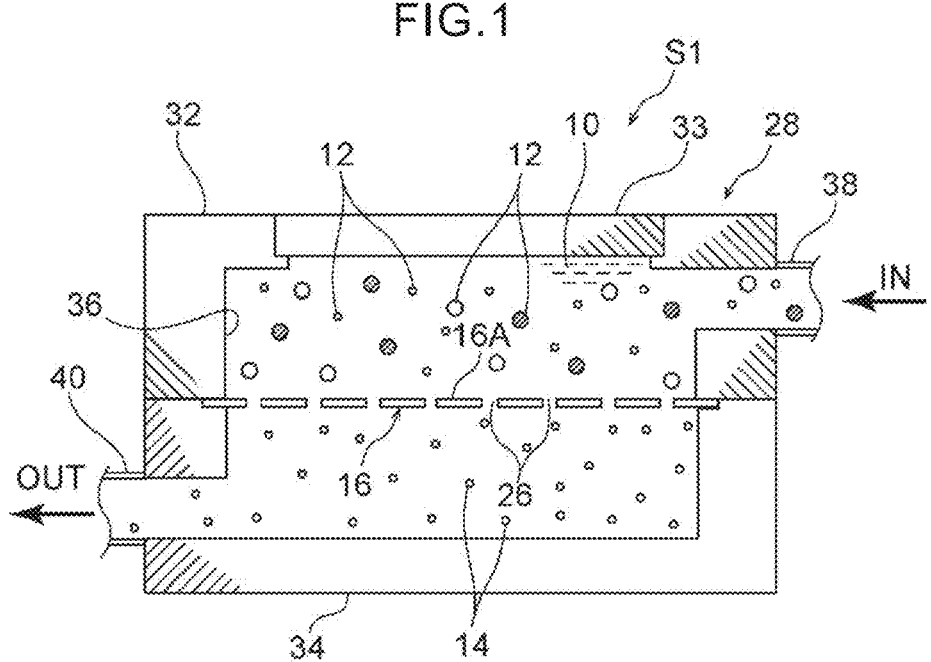

Forms for embodying the present invention are described hereinafter on the basis of the drawings. In the drawings, target cells 12 and a filter 16 and the like are shown in a manner of being enlarged appropriately.

First Embodiment

In the present embodiment, "circulating tumor cells" are circulating tumor cells that are included in blood of a cancer patient, and are rare cells whose cell count is extremely low and that usually exist only as about a few cells within 1 cc of blood. The circulating tumor cells are also called "CTCs" by taking the first letters of "Circulating Tumor Cells" which is the English translation thereof.

"Rare tumor cells" are tumor cells that are rare and are included in a body fluid such as ascetic fluid, peritoneal lavage solution, lymph fluid, cerebrospinal fluid or the like of a cancer patient.

First, in FIG. 1, the filter 16 that is used in the present embodiment and a filter unit 28 in which the filter 16 is incorporated are described.

(Filter)

The filter 16 is a structure in which an extremely large number of pores 26 (a pore density of greater than or equal to $1 \times 10^4 / cm^2$) are formed uniformly or regularly in an extremely thin plate. The density of the pores 26 differs in accordance with the form of the array thereof such as a lattice array, a staggered array, or the like, but is usually $1 \times 10^4$ to $3 \times 10^5 / cm^2$, and is preferably $5 \times 10^4$ to $2 \times 10^5 / cm^2$. Further, the pore diameter of the pore 26 is a size that does not pass target cells therethrough, and can pass through non-target cells, which are body fluid cells other than the target cells such as blood components such as blood cells or the like, or the like. With regard to the size (the length) of human blood cell components, as a result of histogram analysis, the size is around 6 to 7 μm for red blood cells, around 7 to 9 μm for white blood cells, and less than 5 μm for platelets, whereas the size is around 12 to 25 μm for the target cells. Accordingly, the pore diameter of the pores 26 is usually around 7 to 10 μm, and preferably around 8 to 10 μm.

The shape of the filter 16 is not particularly limited provided that is can be placed in a filter ring (a cassette) that is installed in the filter unit 28, but includes shapes such as circular, rectangular and the like for example. Further, the size of the filter 16 can be decided upon appropriately in consideration of physical factors such as the sample (blood) amount, the pore diameter, time, flow speed, withstand pressure and the like, and workability, cost, and the like. For example, in a case of processing 5 ml of blood, the diameter (in the case of a circular filter) or the heightwise and widthwise lengths (in the case of a rectangular filter) are usually around 10 to 15 mm, but the size can be within, non-restrictively and for example, a range of around 5 to 20 mm in accordance with the amount of blood. Further, the thickness of the filter 16 is decided upon appropriately in consideration of the relationships with the pore density, withstand pressure, cost and the like, and usually is 2 to 40 μm, and preferably around 5 to 15 μm.

The filter 16 can be classified into plural types by the material and cross-sectional shape thereof, and, for example, a 3D metal filter 18 (FIG. 3A, FIG. 4A), a 2D metal filter 20 (FIG. 3B), a 2D resin filter 22 (FIG. 3C) and a 3D resin filter 24 (FIG. 9) are given as examples.

Materials of the 3D metal filter 18 and the 2D metal filter 20 include at least any one of, for example, palladium (Pd), platinum (Pt), gold (Au), silver (Ag), iridium (Ir), rhodium (Rh) and ruthenium (Ru). This material may be a metal that is a single substance such as palladium (Pd), platinum (Pt), gold (Au), silver (Ag), iridium (Ir), rhodium (Rh) or ruthenium (Ru), or, for example, may be a palladium (Pd)/nickel (Ni) alloy, a platinum (Pt)/nickel (Ni) alloy, or a gold (Au)/nickel (Ni) alloy, or the like. In the case of an alloy, preferably, the ratio of the above-described metal is large as compared with that of the metal partnered therewith such as nickel or the like. The toxicity of these metals with respect to the target cells 12 is extremely low as compared with that of metals such as nickel (Ni) and the like for example. The reason for this is because leaching out of nickel (Ni) can be prevented due to the toxicity of palladium (Pd) itself being low and due to an alloy of Pd and nickel (Ni) forming a solid solution. Among these, from the standpoints of metal cost and low toxicity, palladium or a palladium (Pd)/nickel (Ni) alloy are preferable. In the case of a Pd/Ni alloy, alloys in which the Pd exceeds 50% (by weight), e.g., an alloy of Pd 80%/Ni 20%, are preferable.

In a case in which the 3D metal filter 18 and the 2D metal filter 20 are fabricated of a Pd and Ni alloy or of Pd or the like, the filters are resistant to organic fixing liquids such as formalin, ethanol and the like, and are advantageous in terms of maintaining the cell shape before and after transfer of the target cells. Moreover, they are acid-resistant and heat-resistant, and, because they are hard and have high durability, they can be washed sterilely, and have the advantage that repeated use thereof is possible. Further, it is difficult for cells to stick thereto even if the filters are not subjected to a surface treatment.

Figure 3A:
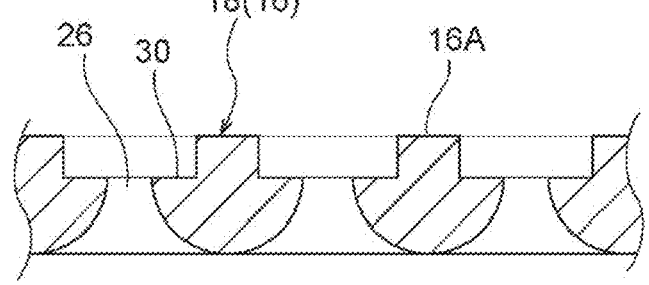
FIG. 3A is an enlarged sectional view showing a 3D metal filter.
Figure 4A:
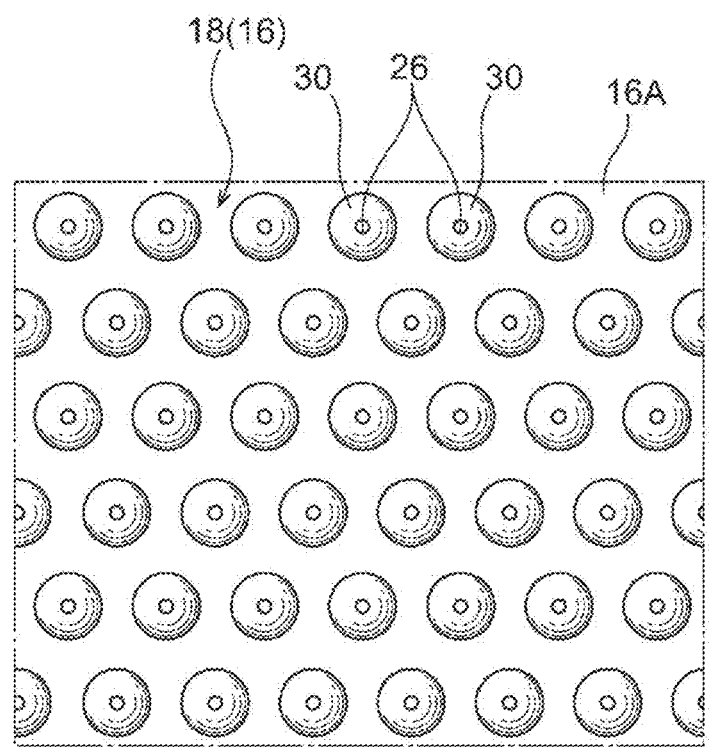
FIG. 4A is an enlarged plan view showing the 3D metal filter.
Figure 8:
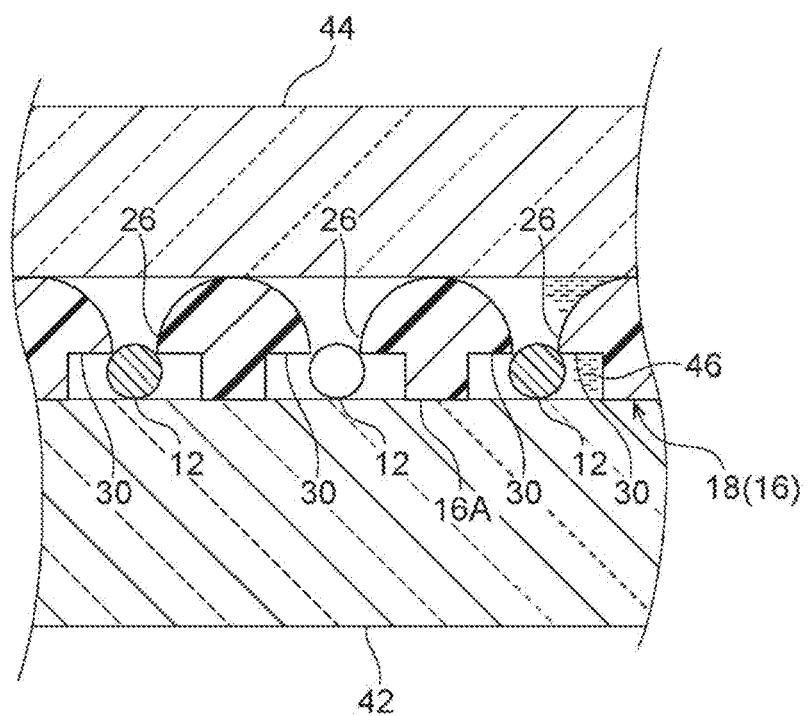
Figure 9:
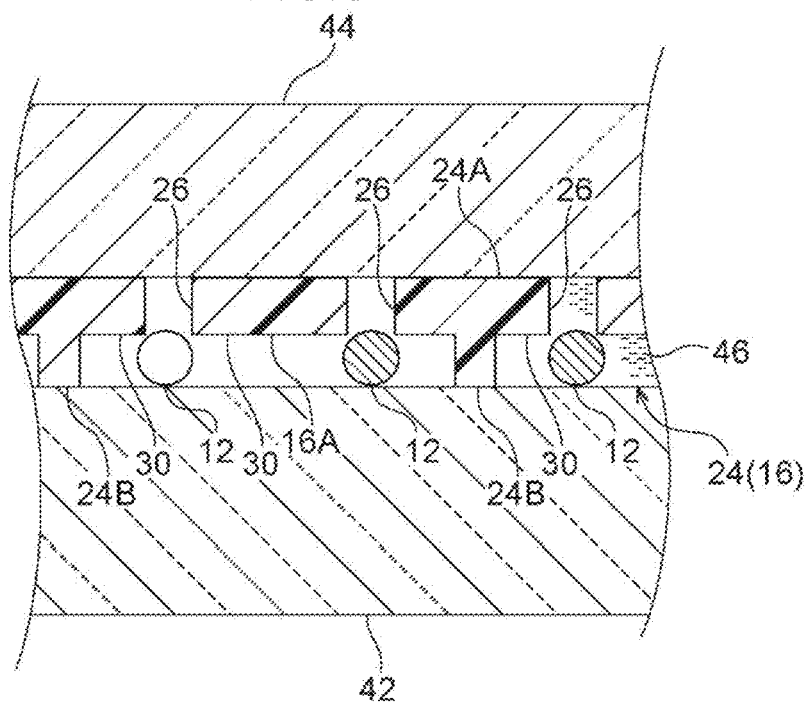

Moreover, as shown in FIG. 3A and FIG. 8, the 3D metal filter 18 has recesses 30 of a size that can capture the target cells 12. The size of the recesses 30 is, non-restrictively and for example, a diameter of 20 to 30 μm and a depth of 5 to 15 μm, and preferably a diameter of 25 to 30 μm and a depth of 10 μm. With a depth that is less than 5 μm, the target cells 12 cannot enter therein. In order for the target cells 12 to substantially completely enter in, it is desirable for the depth of the recesses 30 to be at least around 5 to 15 μm. However, if the depth of the recesses 30 exceeds 15 μm, there is a concern of affecting the recovery rate of the target cells 12 by the transfer. Further, the recesses 30 include shapes that are stepped in the thickness direction, as in the 3D resin filter 24 that is shown in FIG. 9. In other words, the recesses 30 may be surrounded by peripheral walls, or not surrounded.

In order to maintain a high pore density, the recesses 30 may be formed at the upper portions of all of or some of the above-described pores 26. Concretely, the number of recesses is preferably 80 to 100% with respect to the number of the pores 26. It is more preferable that the recesses 30 exist at the upper portions of all of the pores 26. Note that the pore diameter of the pore 26 at the 3D metal filter 18 is the diameter at the position of opening onto the recess 30.

Figure 3B:
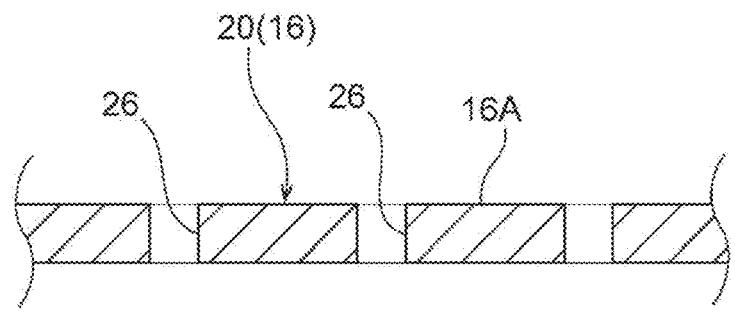
FIG. 3B is an enlarged sectional view showing a 2D metal filter.

In FIG. 3B, the 2D metal filter 20 is a structure that is close to being planar on the whole. The thickness of the 2D metal filter 20 is 10 μm for example. The recesses 30 (FIG.

3A) are not formed in this 2D metal filter 20, but recesses that are of a depth of 5 μm or less (not illustrated) may be provided at the upper portions of the pores 26. This is because the 2D metal filter 20 is a structure that is close to being planar on the whole.

Figure 3C:
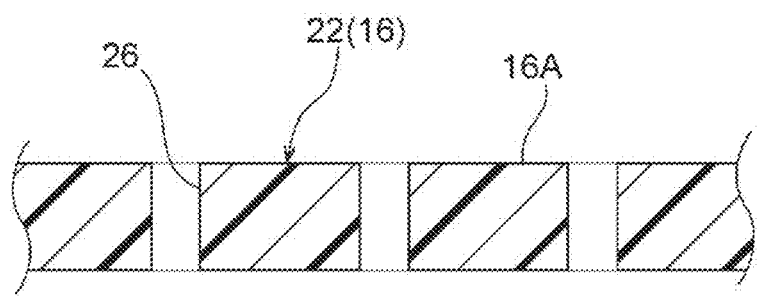
FIG. 3C is an enlarged sectional view showing a 2D resin filter.

In FIG. 3C, the thickness of the 2D resin filter 22 is 15 to 20 μm for example. The recesses 30 (FIG. 3A) are not formed in this 2D resin filter 22, but recesses that are of a depth of 5 μm or less (not illustrated) may be provided at the upper portions of the pores 26. The 2D resin filter 22 is formed of a resin that is epoxy, acrylic, polycarbonate, or the like for example.

In FIG. 9, the 3D resin filter 24 is a structure in which the recesses 30 as well as convex portions 24B are formed at a surface 16A that is at the target cell 12 capturing side of a planar portion 24A that is similar to the 2D resin filter 22 (FIG. 3C). These convex portions 24B are molded integrally with the planar portion 24A while avoiding the pores 26. Further, the convex portions 24B are formed in, for example, dot shapes (pillar shapes), dike shapes, or lattice shapes. In a case of the convex portions 24B being dot-shaped, it is desirable that they exist as dots at three or more places. In a case of the convex portions 24B being dike-shaped, it is desirable that they be provided at two or more places. The height of the convex portions 24B is similar to the depth of the recesses 30 (FIG. 3A) of the 3D metal filter 18.

Figure 4B:
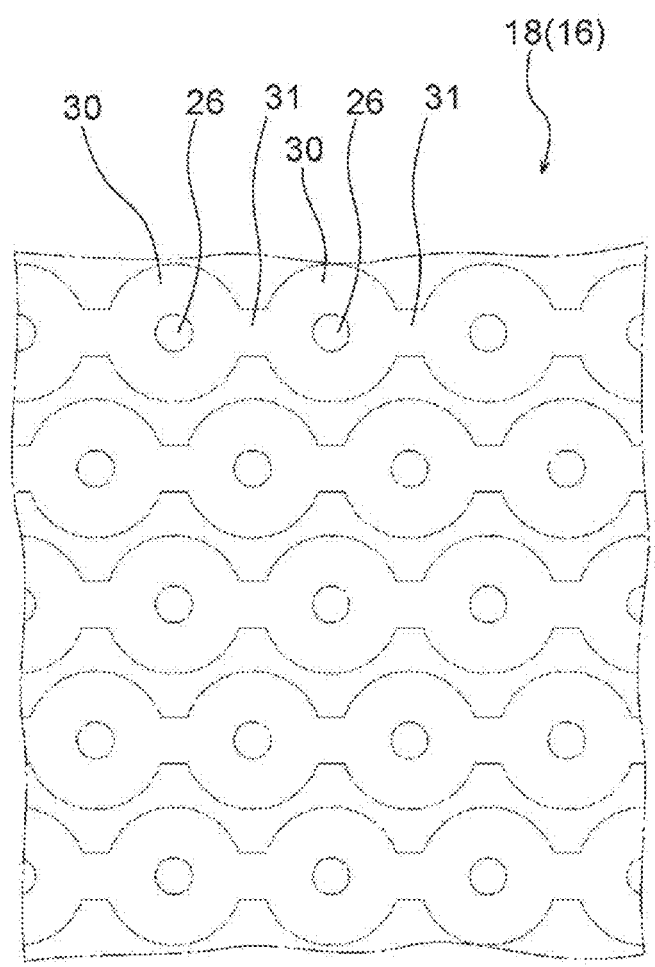
FIG. 4B is an enlarged plan view showing a modified example of the 3D metal filter.
Figure 4C:
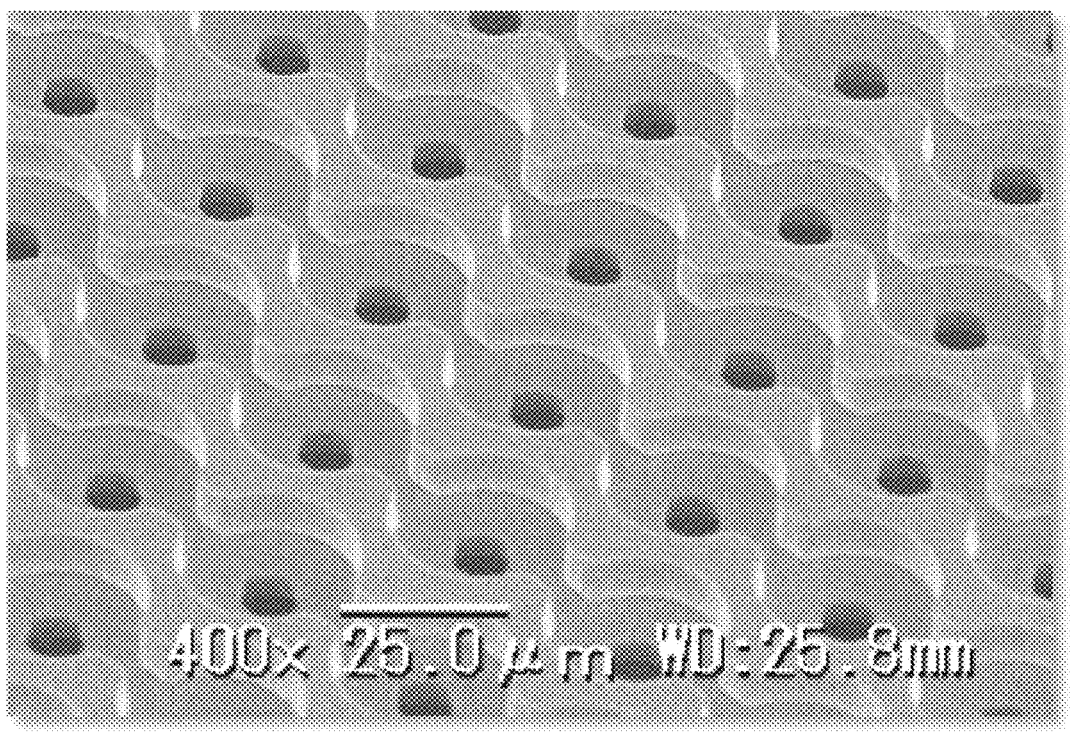
FIG. 4C is a perspective view (a microscope photograph) showing the modified example of the 3D metal filter of FIG. 4B.

In accordance with the 3D metal filter 18, by providing the recesses 30, 1) There can be made to be little contamination of the white blood cells, 2) As compared with a case in which there are no recesses at the upper portions of the pores 26 and the target cells 12 fit in the pores 26 directly, when the recesses 30 do exist, local rotational motion arises at the target cells 12 that have flowed into the recesses 30 from the lateral direction of the filter, and therefore, the fitting into the pores 26 is soft. Namely, by forming a 3D structure that is provided with the recesses 30, the effect is obtained that the strength at which the target cells 12 are captured and fit into the pores 26 can be controlled. 3) Because a buffer solution 46 can collect in the recesses 30, at the time of the transfer of the target cells 12 onto a glass slide 42 due to centrifugal force, it is difficult of the target cells 12 to become dry, and the cell shape can be maintained well (refer to FIG. 6, FIG. 7). Due to the comprehensive effect of these three, concentration of and preservation of the shapes of the target cells 12 are possible, and Papanicolau staining or immunostaining that is carried out afterward can be carried out with high quality. Further, even with a filter that has pores that are slightly large as compared with the pores 26 of a usual pore diameter of 8 μm and that have a pore diameter of 10 that is slightly wide as compared with the target cells 12, there is the possibility that effects that are similar to those described above are obtained. Further, as shown in FIG. 4B and FIG. 4C, it is preferable that communicating paths 31 be provided between the individual recesses 30. The width dimension of these communicating paths 31 is smaller than the diameter of the recesses 30, and is same as the diameter of the pores 26 or is less than or equal thereto, and the depth thereof is the same as that of the recesses 30 or is less than or equal thereto. The reason for providing the communicating paths 31 is because, at the time of superposing the filter 16 on the glass slide 42 after having turned the filter 16 upside-down as is described later, even in cases in which the target cells 12 are fit in the pores 26 and it is difficult for the target cells 12 to drop-down due to the pressure within the recesses 30, the pressure within the recesses 30 escapes at the communication paths 31, and the target cells 12 can easily be made to drop-down. Note that, in FIG. 4C, "400×" is the enlargement magnification, and "WD" is the working distance of the microscope.

It is preferable that the peripheral edge of the filter 16 be edged without pores. Due to an edge portion existing, 1) Packing can be nipped in from above and below the filter 16, and liquid leaking from the filter unit 28 can be prevented, 2) Because it is possible to transfer the target cells 12 at a high density onto a limited region of the glass slide 42, measurement of the number of cells is easy, and moreover, 3) It is possible for the filter 16 to be grasped by tweezers without being damaged.

The filter 16 of the present embodiment can be fabricated by utilizing, for example, the LIGA (Lithogaphie Galavanoformung Abfomung) technique (Tadashi Hattori, Journal of The Surface Finishing Society of Japan, Vol. 62, No. 12, 619-624, 2011; W. Elufeld and H. Lhe, Radiat. Phys. Chem., 45(3): 340-365, 1995). As an example, an electroformed film of the 3D metal filter 18 or the 2D metal filter 20 or the like can be fabricated by a method that includes layering a resist, an absorber (of arbitrary components) and a mask on a substrate, and irradiating ultraviolet rays, X-rays or synchrotron radiation light and forming a resist pattern, and thereafter, carrying out metal plating that carries out electroforming by using the substrate as the electrode, and ending the electroforming at the time when predetermined openings remain, and further carrying out removal of the resist. The 2D resin filter 22 can be fabricated by using a metal mold that is fabricated by electroforming such as the aforementioned LIGA.

At these filters 16, the pores 26 being "arranged regularly" means an arrangement that is as highly dense as possible, and that all of the pores 26 are arrayed with a predetermined regularity. For example, a lattice-shaped array, a staggered lattice array (FIG. 4), a radial array, a concentrically circular array, and the like are included as such regularity.

(Filter Unit)

Figure 2:
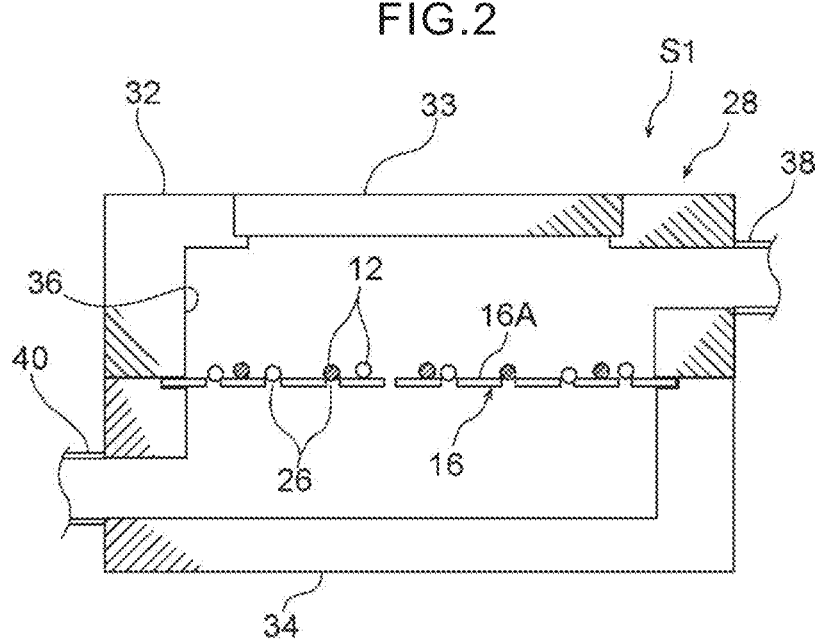

In FIG. 1 and FIG. 2, the filter unit 28 is a structure in which a flow path 36 is formed at the interior by an upper body 32 and a lower body 34. The filter 16 is removably placed between the upper body 32 and the lower body 34 for example. The flow path 36 is perpendicular to the filter 16. The filter 16 may be fixed to the upper body 32 or the lower body 34 via an unillustrated filter cassette or the like.

An entrance portion 38 is provided at the upper body 32, and an exit portion 40 is provided at the lower body 34. A sample liquid 10 that is blood or a body fluid is supplied from the entrance portion 38. The sample liquid 10, which has passed-through the pores 26 of the filter 16 and mainly contains non-target cells 14, is discharged from the exit portion 40. In the supplying of the sample liquid 10, it is good to utilize pressurization using a pump or the like, but the supplying may be the application of negative pressure to the exit portion 40. Further, the weight of the sample liquid 10 itself may be utilized. Note that a ceiling portion 33 that can open and close may be provided at the upper body 32.

From the standpoints of ease of machining and cost, it is preferable that the entire filter unit 28 be formed of a resin that is acrylic or the like or a polymer. If the filter unit 28 is of a transparent material, it is preferable because the flow-down speed of the liquid can be observed.

Although not illustrated, in addition to the filter unit 28, a reservoir unit, a flow rate adjusting unit, and a discharged liquid recovery unit (a liquid storage base) can be further included.

(Method of Preparing Glass Slide Specimen of Cells)

The method of preparing a glass slide specimen of cells relating to the present embodiment has a first step S1 through a fourth step S4.

In FIG. 1 and FIG. 2, in the first step S1, the target cells 12, which are at least one of circulating tumor cells within blood or rare tumor cells within a body fluid, are separated from the non-target cells 14 and captured by the filter 16. As shown in FIG. 1, when the sample liquid 10 is injected from the entrance portion 38 into the flow path 36 that is within the filter unit 28, the target cells 12 that are contained in the sample liquid 10 are captured by the filter 16, and the non-target cells 14 and moisture pass-through the pores 26 of the filter 16 and are discharged-out from the exit portion 40. As a result, as shown in FIG. 2, there is a state in which the target cells 12 are captured by the filter 16.

Here, the amount (volume) of the sample liquid 10 is usually 0.2 to 20 ml, and is preferably 5 to 10 ml. Usually, the sample liquid 10 (blood in particular) is filtered after being diluted 2 to 20 times for example by phosphate-buffered saline (PBS) (PBS containing 0.25 to 1 ml of EDTA in accordance with the purpose). Although usually unnecessary for a sample amount of 5 to 20 ml, the following pretreatment may be carried out in cases in which the amount of blood is large (20 to 50 ml).

In the pretreatment, for example, a hemolytic agent of an ammonium chloride base is added to the sample liquid 10 such as blood or the like, and the red blood cells are removed, and a liquid, in which the target cells 12 such as CTCs or rare tumor cells or the like are concentrated 10 times or more, is led to the filter unit 28, and due thereto, the filtering time can be shortened without raising the filtering speed. In this case, the white blood cells can be removed in a state in which the flow speed of the 3D metal filter 18 is greatly slowed, and therefore, the target cells 12 are captured softly in the recesses 30 of the 3D metal filter 18 without fitting deeply into the pores 26. In a case in which the pretreatment of the present embodiment is also used, as compared with a case in which the pretreatment is not utilized, the shear stress applied to the target cells 12 that are captured at the 3D metal filter 18 is reduced, enucleated cells that have hardly any cytoplasm are reduced, and better maintenance of the cell shape can be expected. However, on the other hand, there is the concern that such a pretreatment will lead to a loss of the target cells 12.

The present method is a simple method of injecting the sample liquid 10 into the filter unit 28 and carrying out filtering by pressurization by a pump. However, by using the 3D (or the 2D) metal filter 18 that has an extremely high pore density (e.g., $5 \times 10^4$ to $1.5 \times 10^5/cm^2$), allowable, sufficient and rapid processing can be achieved. For example, a sample (whole blood) of around 5 to 7 ml can be processed in around 30 minutes including washing. Phosphate-buffered saline (PBS) is used as the washing liquid, but EDTA may be contained in the washing liquid as needed.

Between the first step S1 and the second step S2, the target cells 12 may be stained by a labeled antibody. Concretely, the target cells 12 may be stained by using a fluorescent labeled antibody that specifically joins to the target cells 12, for example, an antibody mixture of Alexa 488 labeled Anti-Keratin antibody, PE labeled Anti-EpCAM antibody, Alexa 647 labeled Anti-CD45 antibody that specifically joins to white blood cells, and the like, and fluorescent stains for nuclear staining (Hoechst). These stainings can be carried out directly on the 3D metal filter 18 that is fixed to the filter unit 28. Due thereto, between the second step S2 and the third step S3 that are described later, the number and the like of the target cells 12 that are captured on the filter 16 can be counted by using a fluorescent microscope.

Figure 5:
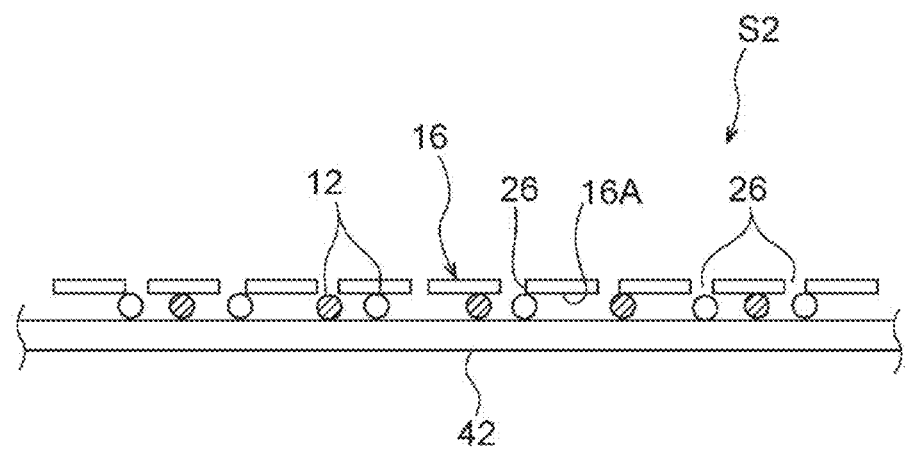
Figure 6:
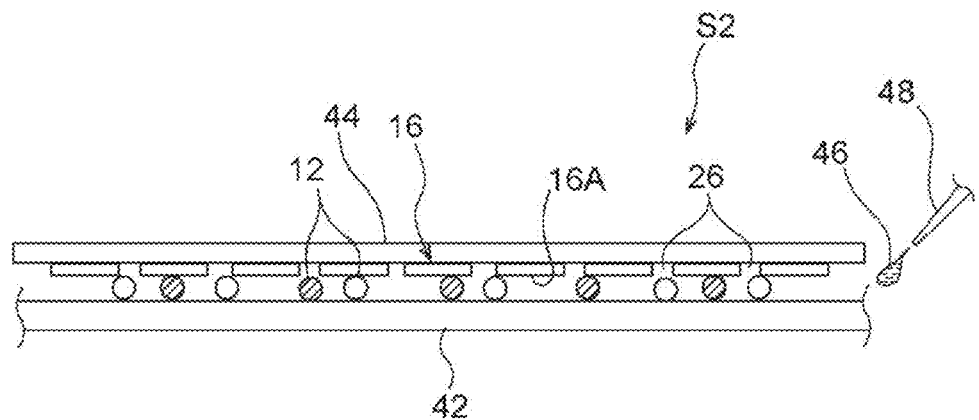
Figure 7:
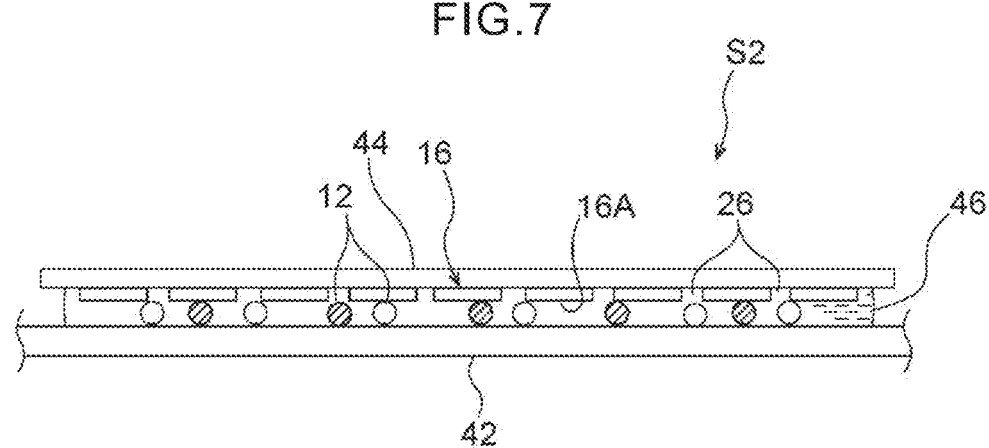

In FIG. 5 through FIG. 7, in the second step S2, the surface 16A at the target cell 12 capturing side of the filter 16 is made to face the glass slide 42, this filter 16 is superposed on the glass slide 42 (FIG. 5), a cover member 44 is placed on the filter 16 (FIG. 6), and the target cells 12 that are between the filter 16 and the glass slide 42 are immersed in the buffer solution 46 (FIG. 6, FIG. 7).

In the state in which the filter 16 is fixed to the filter unit 28 (FIG. 2), the surface 16A at the target cell 12 capturing side of this filter 16 is the surface at the upper side. Because the surface 16A at the capturing side is made to face the glass slide 42, either the filter 16 is superposed on the glass slide 42 after the filter 16 is turned upside-down, or the glass slide 42 is superposed on the filter 16, and the filter 16 and the glass slide 42 are turned upside-down. In the state in which the filter 16 is superposed on the glass slide 42, the surface 16A at the capturing side of the filter 16 is the surface at the lower side. In this state, the target cells 12 that are captured by the filter 16 are positioned between this filter 16 and the glass slide 42.

As shown in FIG. 8, in a case in which the filter 16 is the 3D metal filter 18, the target cells 12 settle into the recesses 30, and therefore, there is little stress that deforms the cells, and there is little cell damage. As shown in FIG. 9, also in a case in which the filter 16 is the 3D resin filter 24, a gap between the glass slide 42 and the surface 16A at the capturing side of the filter 16 is ensured by the recesses 30 that are formed by the convex portions 24B. Therefore, there is little stress that deforms the cells, and there is little cell damage, but the hardness is poor and there are drawbacks with respect to durability as compared with the 3D metal filter 18.

It is preferable that the cover member 44 be larger than the filter 16 for example, and that the cover member 44 cover the filter 16 with leeway overall. The material of the cover member 44 is glass or resin or the like.

In order to immerse the target cells 12 in the buffer solution 46, for example, before the cover member 44 is superposed on the filter 16, the target cells 12 are immersed in the buffer solution 46, and thereafter, the cover member 44 is gently superposed thereon. As shown in FIG. 6, the buffer solution 46 may be injected between the cover member 44 and the glass slide 42 by using a pipette 48. In either case, the filter 16 and the buffer member 44 are held on the glass slide 42 by the surface tension of the buffer solution 46.

The buffer solution 46 is, for example, a saline solution or a phosphate buffered saline solution, but is not limited to these, and, from the standpoint of preventing drying of the target cells 12 as well, a polymer that can impart viscosity to the buffer solution and is nontoxic to cells such as a polysaccharide or the like, or the like may be added.

Between the first step S1 and the second step S2, the target cells 12 can be quadruple stained with Anti-Keratin antibody, Anti-EpCAM antibody, Anti-CD45 antibody, and a nuclear stain (Hoechst), and, before proceeding on to the third step S3, the number or the like of the target cells 12 (Keratin+/EpCAM+/CD45−/Hoechst+) captured on the filter 16 can be counted.

Figure 10:
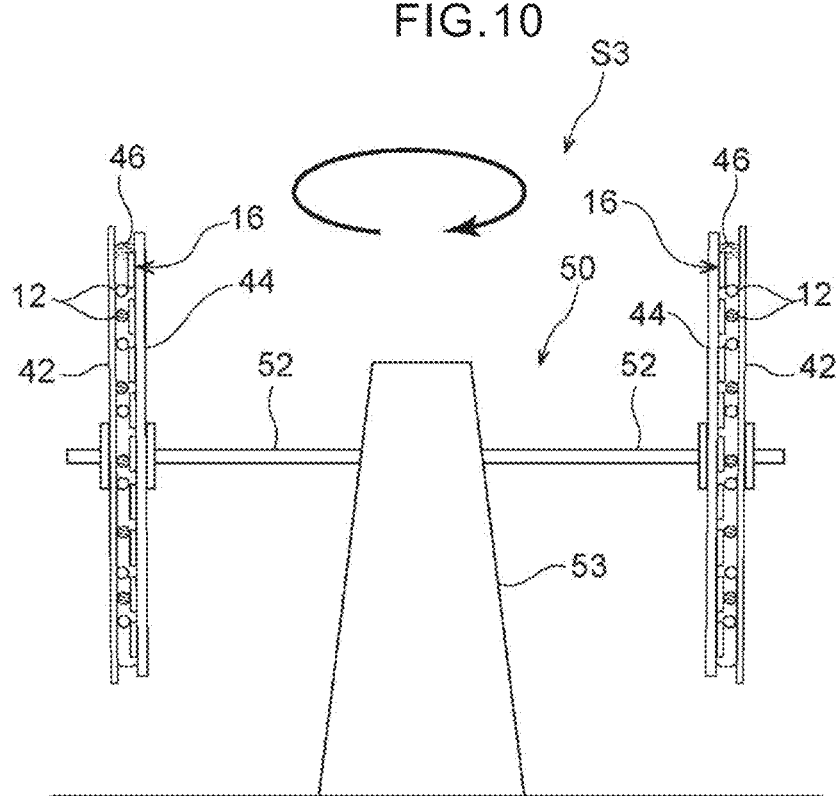

In FIG. 10, in the third step S3, the target cells 12 are transferred onto the glass slide 42 by using cellular adhesive force onto a matrix (not illustrated) that is coated on the glass slide 42, under the action of centrifugal force for example on the target cells 12 that are between the filter 16 and the glass slide 42. Concretely, the filter 16 and the cover member 44 are superposed, and the glass slide 42, at which the target cells 12 have been immersed in the buffer solution 46, is attached to an arm portion 52 of a swing-rotor-type centrifuge 50 for example, and a rotating shaft 53 to which this arm portion 52 is fixed is rotated. At this time, due to the glass slide 42 being placed at the radial direction outer side of the centrifuge 50, centrifugal force can be applied to the target cells 12 in a direction orthogonal to the surface of the filter 16 and the surface of the glass slide 42.

Figure 11:
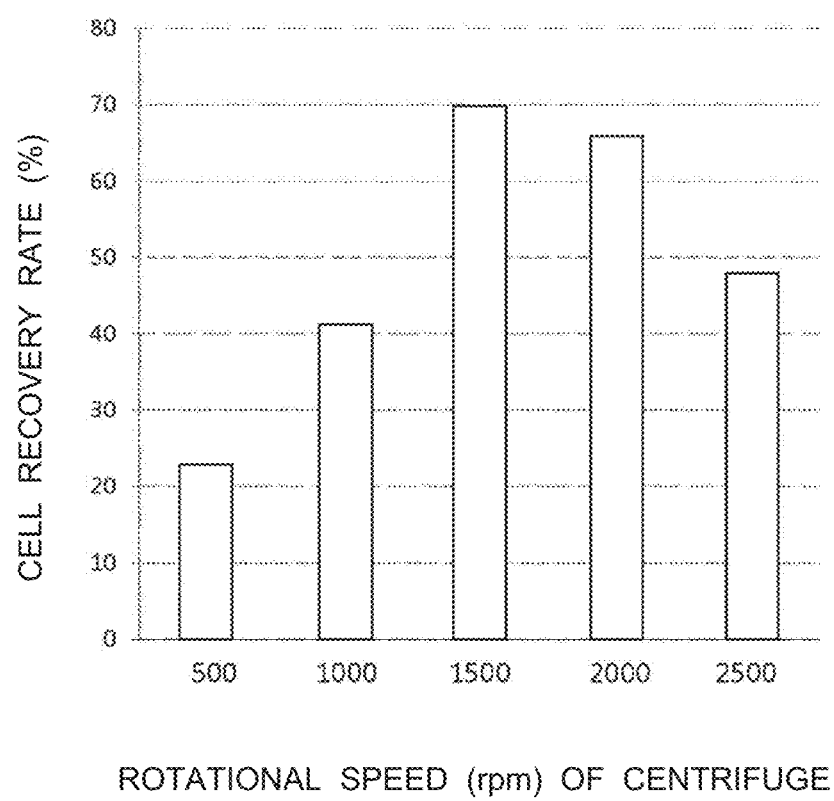

As shown in FIG. 11, if the rotational speed of the centrifuge 50 is high, the recovery rate of the cells increases. The recovery rate is the ratio of the number of cells, which, after use of the centrifuge 50, are transferred to the glass slide 42 and their shapes preserved well, with respect to the number of cells which are captured by the filter 16 before the centrifuge 50 is used. From FIG. 11, a rotational speed of 1500 to 2000 rpm is desirable. This is because, if the rotational speed is too much higher than this, effects on cell damage are great.

Figure 12:
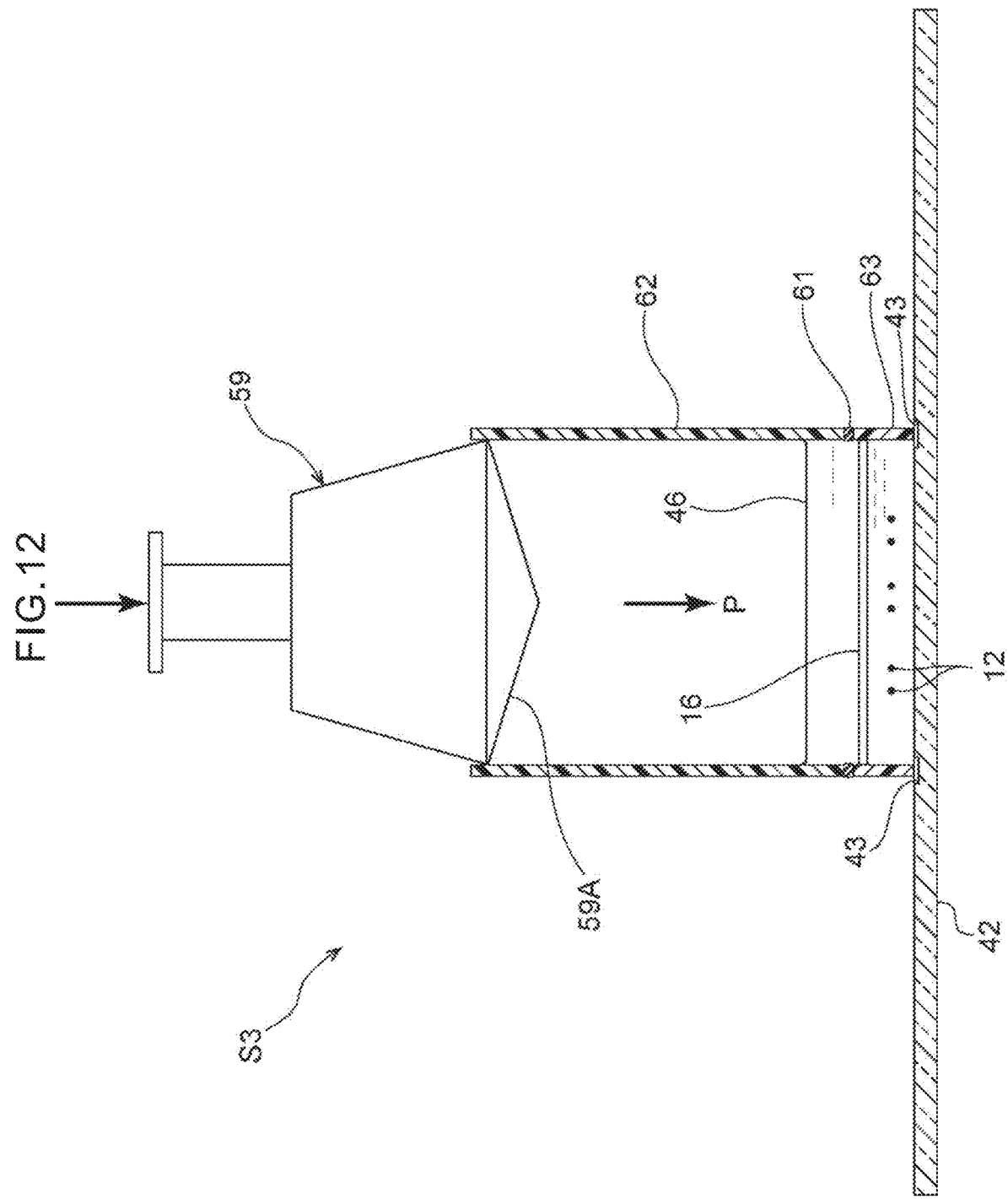

Note that, in the third step S3, the adherability of the cells to the glass slide 42 under pressurization such as air pressure or the like may be utilized on the target cells 12 rather than centrifugal force. Concretely, as shown in FIG. 12, the filter 16 (a 2D filter), which has been removed from the filter unit 28 in the second step S2, may be allowed to gently put on the glass slide 42 whose cell adherability has been increased due to various types of substances being coated on the surface thereof such as a hydrophilic treatment by plasma or the like on the surface or the like, and thereafter, light air pressure may be applied manually by a cylinder-type pressurizing instrument 59 that is cylindrical or the like, and the adhesive performance between the cells and the matrix may be utilized, and the target cells 12 transferred onto the glass slide 42 in a stamped manner. Rubber 59A is provided on the distal end, which faces the interior of a tubular body 62, of the cylinder-type pressurizing instrument 59. A filter cassette 63 that has the filter 16 is placed between the tubular body 62 and the glass slide 42. A silicon gasket 61 is provided between the tubular body 62 and the filter cassette 63.

In a case in which the target cells 12 are cells that have been fixed, the glass slide 42, which is commercially available and whose surface has been subjected to a hydrophilic treatment by plasma or the like or on whose surface various types of substances have been coated, may be used. Further, in order to promote transfer of the target cells 12 onto the glass slide 42, an appropriate number of grooves 43 of a width of 1 to 5 μm and a depth of 1 to 5 μm may be provided by cutting or the like in the surface of the glass slide 42, and a drainage opening may be formed, and a slow liquid flow by pressurization from above may be created, or the like.

Figure 13:
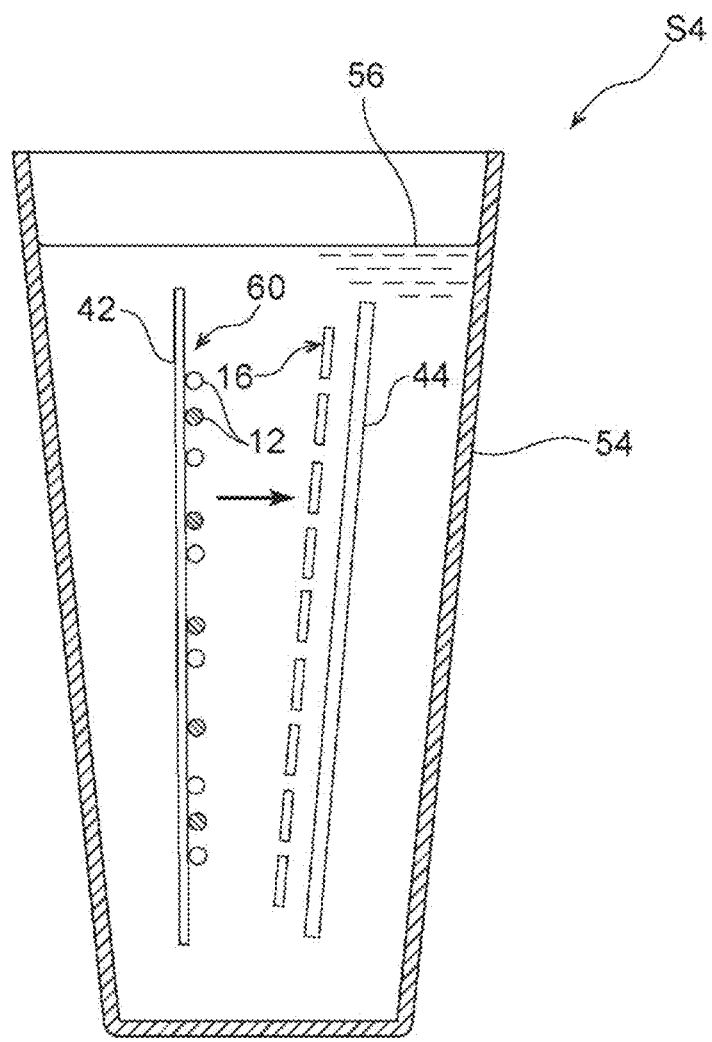

In FIG. 13, in the fourth step S4, by immersing the glass slide 42 in a container 54 in which a preservation liquid 56 is stored, the cover member 44 and the filter 16 are peeled-off naturally and preserved without damaging the target cells 12. The preservation liquid 56 is various types of fixing liquids that correspond to the staining thereafter, for example, a fixing liquid that is 10% formalin or is 95% ethanol or the like, and moreover is a buffer solution, but is not limited to this. By immersing the glass slide 42 in the preservation liquid 56, the surface tension of the buffer solution 46 loses-out to the surface tension of the preservation liquid 56, and the filter 16 and the cover member 44 naturally peel-off from the glass slide 42. Therefore, damage to the target cells 12 in a process of peeling the cover member 44 off is kept to a minimum. In the third step S3, the target cells 12 are firmly transferred to the glass slide 42, and therefore, even if the filter 16 and the cover member 44 peel-off, the target cells 12 are held on the glass slide 42.

Figure 14:
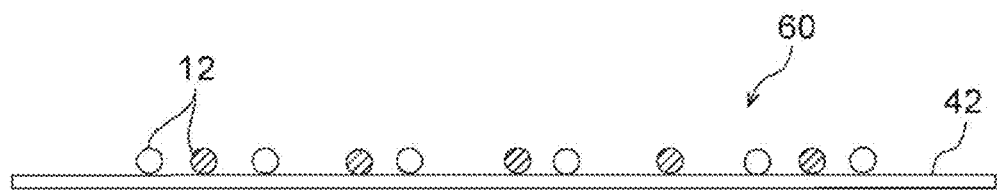

Due thereto, as shown in FIG. 14, a glass slide specimen 60 in which the target cells 12 are fixed to the glass slide 42 is obtained.

In accordance with the method of preparing a glass slide specimen of cells relating to the present embodiment, by using the filter 16, the target cells 12 (circulating tumor cells or rare tumor cells) within the sample liquid 10 can be concentrated, separated, and captured by utilizing the difference in size between them and the non-target cells 14 (e.g., blood cells).

Further, at the time when the target cells 12 that have been captured are transferred softly onto the glass slide 42 by using the cell adherability under the application of centrifugal force or under pressurization by air pressure or the like, because the target cells 12 are immersed in the buffer solution 46 that has collected in the recesses 30 of the filter 16, at the time when the target cells 12 are transferred to the glass slide 42, it is difficult for the target cells 12 to be crushed and to dry-out, and therefore, cell damage can be kept to a minimum.

Further, the glass slide specimen 60 at which the target cells 12 are transferred onto the glass slide 42 is prepared by immersing the glass slide 42 in the container 54 in which the preservation liquid 56 is stored, and causing the cover member 44 and the filter to peel-off naturally. The glass slide specimen 60 can be stored for a long time in the preservation liquid 56 at room temperature or at 4° C.

Even in a case in which the target cells 12 are stained by a labeled antibody between the first step S1 and the second step S2, and the number of stained target cells 12 is counted by using a fluorescent microscope, these target cells 12 can be recovered and transferred from the filter 16 onto the glass slide 42 easily and in a stable state.

Second Embodiment

Figure 17:
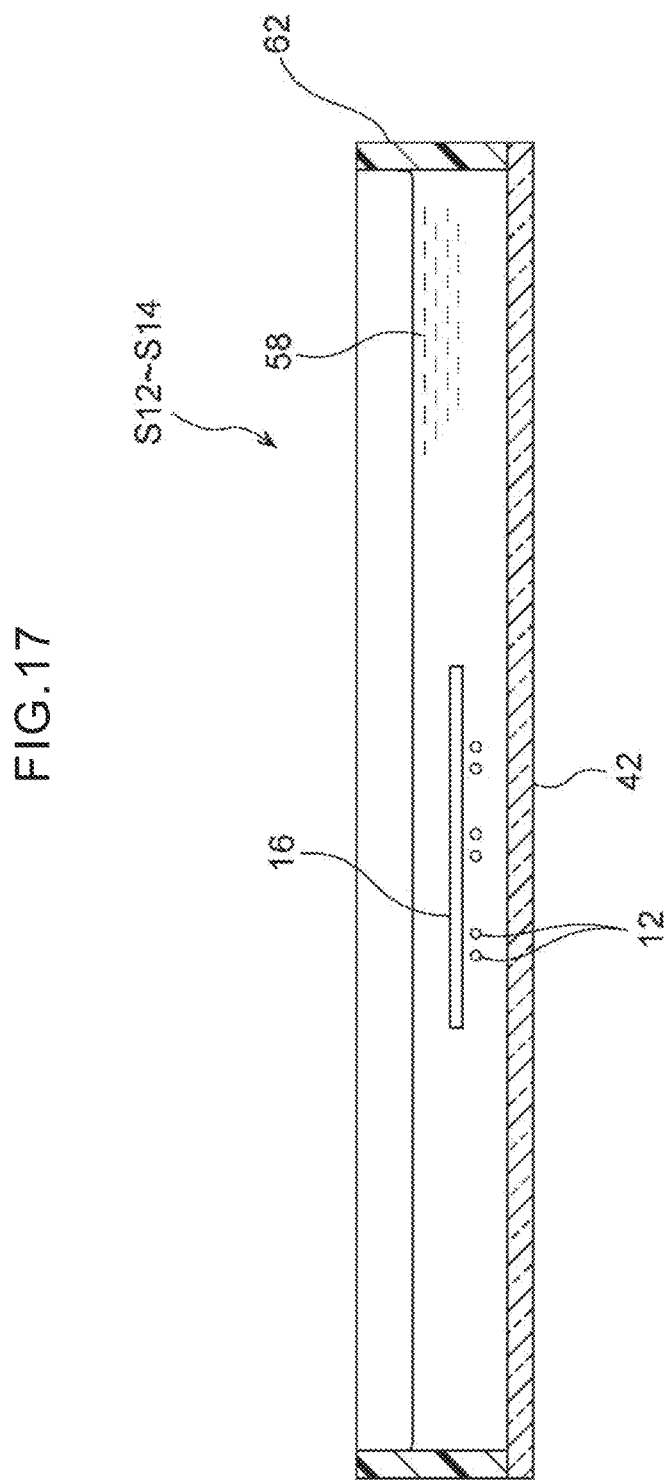
FIG. 17 is a cross-sectional view that relates to a second embodiment and shows a state in which, in a case of transfer under survival conditions, the target cells migrate on their own from the filter onto the glass slide and adhere thereto.

In FIG. 17, a method of preparing a glass slide specimen of cells relating to the present embodiment has the first step S1 (refer to FIG. 1 as well) that is similar to that of the first embodiment, and has a second step S12 through a fourth step S14. Portions that are the same as the first embodiment are denoted by the same reference numerals in the drawings, and description thereof is omitted.

In the first step S1, fixing and a surfactant treatment are not carried out on the target cells 12, and processing moves on to the second step S12 with the target cells 12 still living. In the second step S12, the filter 16 that has been removed from the filter unit 28 is allowed to stand on the glass slide 42 on whose surface an adhesion promoting substance such as type I collagen or the like has been coated, and thereafter, a culture solution 58 is added immediately, and the target cells 12 are adhered while still living for example.

In the third step S13, due to the target cells 12 being heated for 1 to several hours at 37° C. within a $CO_2$ incubator, the migration capability of the cells is utilized, and the target cells 12 are sufficiently adhered onto the glass slide 42, and are transferred thereon under pressurization or not under pressurization.

In the fourth step S14, the tubular body 62 is placed on the glass slide 42 so as to make a culture dish, and a sufficient amount of the culture solution 58 is added to this culture dish, and the filter 16 is made to float in the culture medium and is removed from the glass slide 42. Due thereto, without applying an external force such as centrifugal force or air pressure of the like to the cells, cell damage is kept to a minimum, and the target cells 12 can be recovered on the glass slide 42 while still living (FIG. 17). In a case of transfer of the target cells 12 under survival conditions, these target cells 12 migrate themselves from the filter 16 onto the glass slide 42 and adhere thereto.

In the fourth step S14 of FIG. 17, the filter 16 and the cover member 44 are removed, and the target cells 12 that have been transferred to the glass slide 42 are fixed by a fixing liquid such as formalin or ethanol for example, and thereafter, can be used in Papanicolau staining or immunostaining. Further, the target cells 12 can be cultivated for a short time within the culture dish. Namely, the target cells can be utilized as cells for staining or for cultivation.

In accordance with this method of preparing a glass slide specimen of cells, in the same way as in the first embodiment, by the filter 16 (which is made of metal or made of resin for example), the difference in size between the target cells 12 (circulating tumor cells or rare tumor cells) and the non-target cells 14 (e.g., the blood cells) within a sample liquid is utilized, and the target cells 12 can be easily, rapidly and highly efficiently separated and captured. However, in a case of collecting the former that have little damage and that are still living, as compared with the first embodiment, a heating operation within a $CO_2$ incubator is necessary, and therefore, a time of several hours to several days is required for cell recovery, and a time of several days to several weeks is required for cell cultivation.

[Utilization of Glass Slide Sample]

Figure 15:
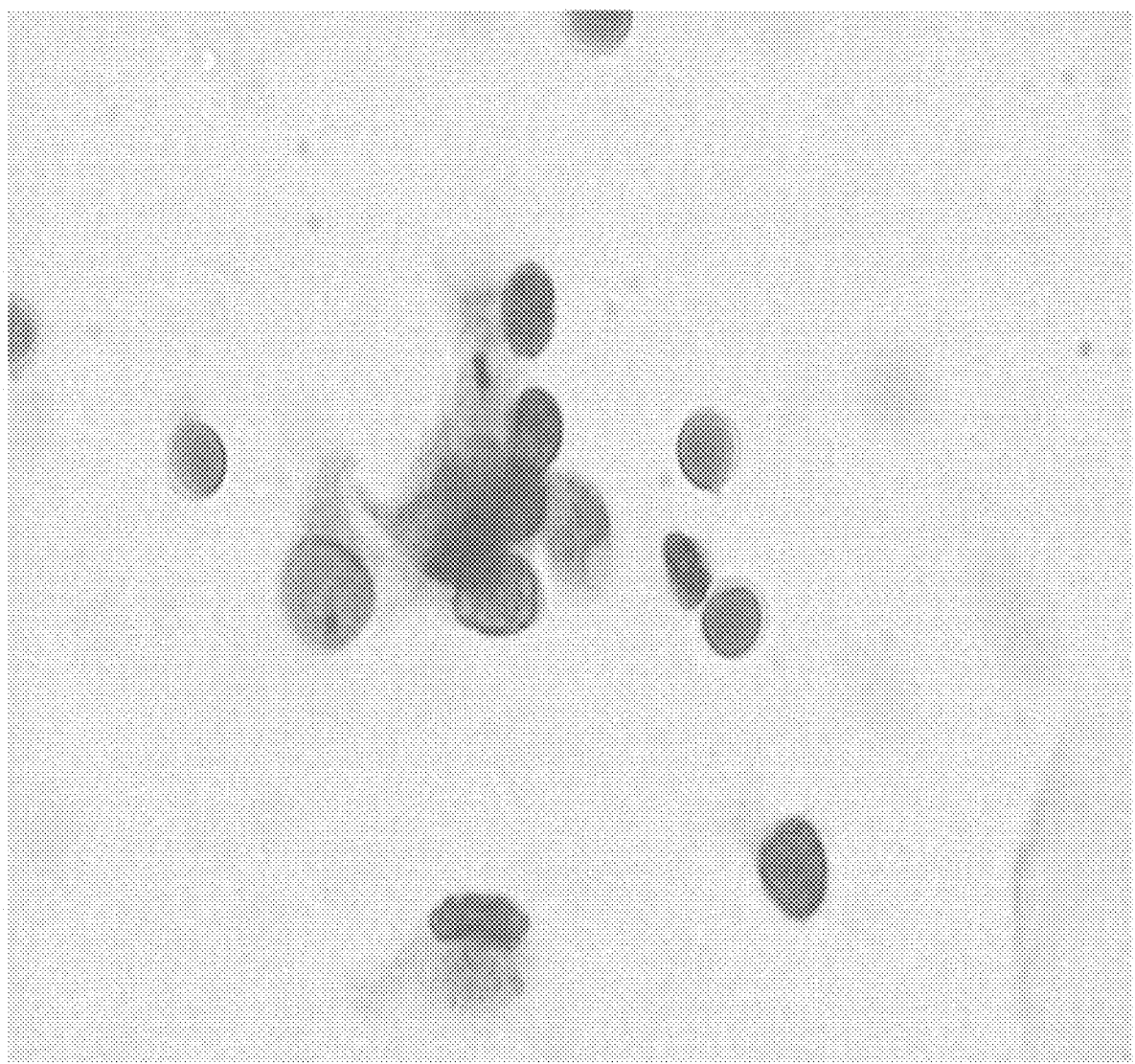
Figure 16:
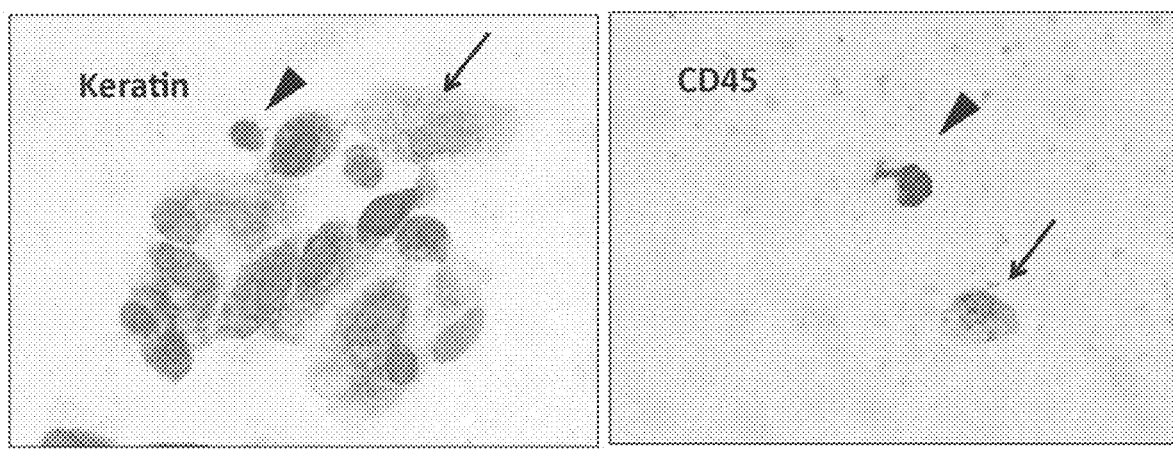

By using the glass slide specimen 60 of the target cells 12, for example, Papanicolau staining (FIG. 15) or immunostaining (the IHC method) (FIG. 16) can be carried out as routine work of a laboratory. FIG. 15 is a microscope photograph of cells on which Papanicolau staining has been carried out. The preserving of the cell shape is good, such as the chromatin pattern is clear and the cytoplasm also remains and the like, and therefore, a pathologist or a cytologist can observe the target cells as in cytodiagnosis, and accurate and objective evaluation of CTCs is possible. FIG. 16 is a microscope photograph of cells on which immunostaining by the IHC method has been carried out, and shows the results of staining with cytokeratin and CD45. In addition to evaluation in accordance with the cell shape, evaluation in accordance with the immunostaining is added, and therefore, the judgment of CTCs is even more accurate. Further, immunostaining that is needed for a companion diagnosis such as HER2, ER, PgR staining or the like also is possible.

(Method of Extracting DNA or RNA)

Figure 18:
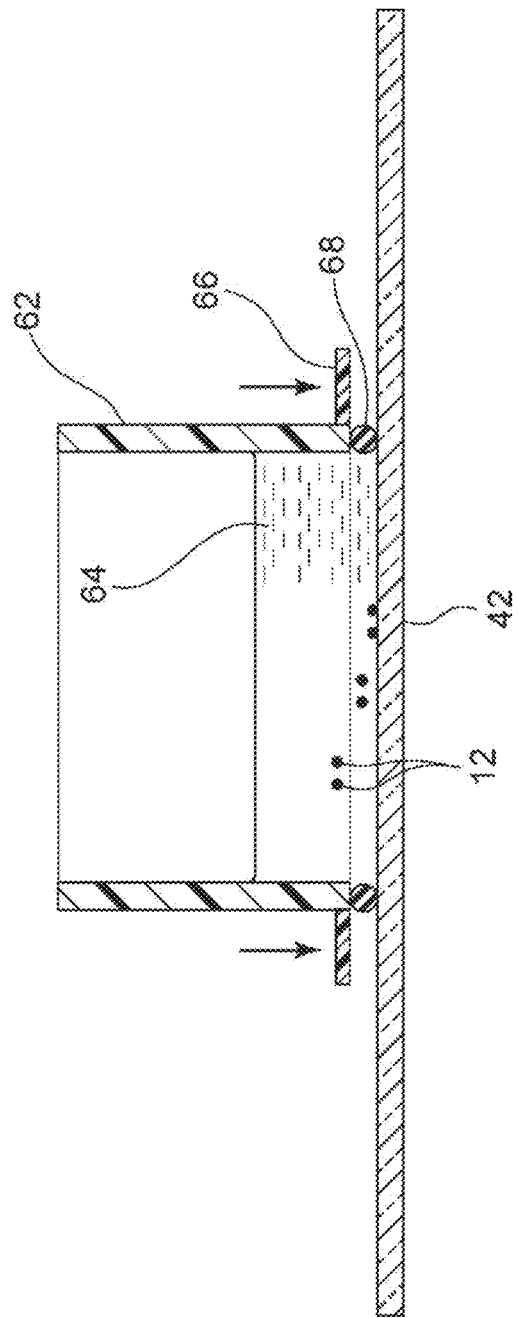
FIG. 18 is a cross-sectional view showing a method of setting a tubular body that is cylindrical tightly on the glass at the periphery of the target cells that have been transferred onto the glass slide, and adding a DNA extraction liquid and extracting DNA.
Figure 19:
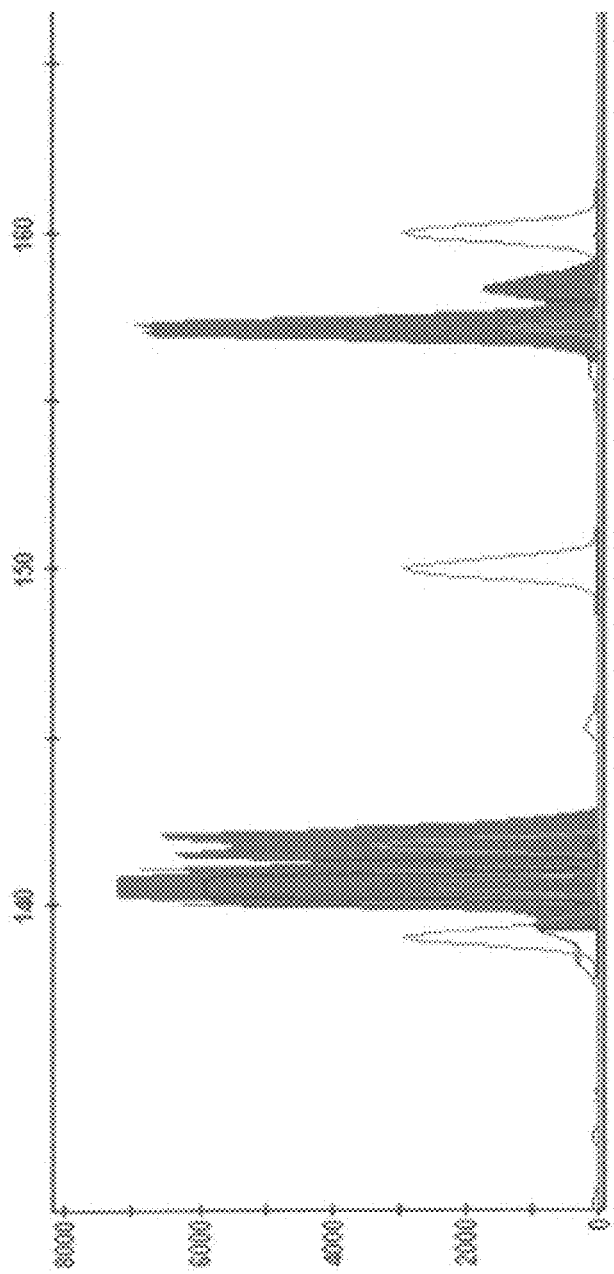
FIG. 19 is a graph showing an example of genetic analysis using the DNA extracted from the target cells on the glass slide.

On the glass slide specimen 60, DNA or RNA can be extracted from the target cells 12, and genetic analysis can be carried out by a known method. FIG. 18 shows a state in which the tubular body 62 is placed on the glass slide specimen 60, and the periphery of the target cells 12 that have been transferred onto the glass slide 42 is fit tightly to and surrounded by the tubular body 62 that is cylindrical and is made of resin for example. A DNA or RNA extraction liquid 64 is maintained for a predetermined time within this tubular body 62. Concretely, a DNA extraction liquid such as Proteinase K soln or the like for example is added into the tubular body 62, and is incubated for 60 minutes (or more) at 56° C., and the DNA is extracted. As needed, the DNA is purified, and, by using this, various types of genetic analysis by the PCR method or the like can be carried out (FIG. 19). Note that the material of the tubular body 62 is not limited to resin, and may be another material such as a metal or the like. In order for the DNA or RNA extraction liquid 64 to be stored without leakage and incubated at 56° C. for a given period (e.g., 1 to 4 hours), as shown in FIG. 18, there may be a structure in which a handle 66 that applies pressure for tight fitting is provided at the side portion of the tubular body 62, and a rubber 68 (a sealing member) that is annular is placed at the bottom portion of the tubular body 62, and pressure is applied to the handle 66, and the tubular body 62 is made to fit tightly to the glass slide 42.

RLT soln can be used as the RNA extraction liquid. The RNA extraction liquid is added into the tubular body 62 that is on the glass slide specimen 60, the RNA is purified by using an RNeasy Kit or the like as appropriate, and various types of genetic analysis can be carried out by the PCR method.

In this way, due to the preparing of a glass slide specimen of the target cells 12, the present technique can be utilized not only for measurement of the number of cells, but also can be used easily and inexpensively as liquid cytodiagnosis (a liquid biopsy) that is needed for companion diagnosis such as cytologic diagnosis or genetic analysis or the like that uses immunostaining of the target cells 12.

In the method of preparing a glass slide specimen of cells relating to the above-described embodiment, the equipment that is needed are only the filter 16 that is inexpensive, safe and disposable, a filtering device, a simple syringe pump, the centrifuge 50 that is a tabletop centrifuge and is low-speed, a coating glass slide (the glass slide 42) that is disposable, the syringe-type pressurizing instrument 59 that is compact and cylindrical, and a DNA/RNA collection instrument (the tubular body 62). This transfer/recovery device and system of target cells such as CTCs or the like onto a glass slide make examination of CTCs and the like in a laboratory of a general hospital possible, and have unprecedented polyfunctionality as detection, recovery and analysis techniques of target cells such as CTCs or the like.

Other Embodiments

Although examples of embodiments of the present invention have been described above, embodiments of the present invention are not limited to the above, and, other than the above, the present invention can of course be implemented by being modified in various ways within a scope that does not depart from the gist thereof.

For example, between the first step S1 and the second step S2, S12, counting of the number of target cells using staining by a fluorescent labeled antibody and a fluorescent microscope does not have to be carried out, and rather, more accurate measurement is possible on the glass slide specimen. Further, when labeled antibody staining is not carried out at this stage, better trends are seen also in the results of immunostaining after the preparation of the glass slide specimen in the fourth step S4, S14 and thereafter.

The disclosure of Japanese Patent Application No. 2016-145568 that was filed on Jul. 25, 2016 is, in its entirety, incorporated by reference into the present specification. All publications, patent applications, and technical standards mentioned in the present specification are incorporated by reference into the present specification to the same extent as if such individual publication, patent application, or technical standard was specifically and individually indicated to be incorporated by reference.

What is claimed is:

1. A method of preparing a glass slide specimen of cells that has a filter that has recesses, which capture target cells that are at least one of circulating tumor cells within blood or rare tumor cells within a body fluid, and pores that are formed in the recesses and that pass non-target cells therethrough, the method comprising:

a first step of separating, via the filter, the target cells from the non-target cells and capturing the target cells;
a second step of superposing the filter on the glass slide such that a surface of the filter, at a side at which the target cells are captured, faces the glass slide, placing a cover member on the filter, and immersing the target cells, which are between the filter and the glass slide, in a buffer solution;
a third step of transferring the target cells, which are between the filter and the glass slide, onto the glass slide under application of centrifugal force or under pressurization by air pressure; and
a fourth step of, by immersing the glass slide in a container in which a preservation liquid is stored, causing the cover member and the filter to peel-off naturally from the glass slide and preserving the target cells, without impairing the target cells,
wherein a groove of a width of 1 to 5 µm and a depth of 1 to 5 µm is provided in the surface of the glass slide, and the groove is a drainage opening.

2. A method of preparing a glass slide specimen of cells that has a filter that has recesses, which capture target cells that are at least one of circulating tumor cells within blood or rare tumor cells within a body fluid, and pores that are formed in the recesses and that pass non-target cells therethrough, the method comprising:
a first step of separating, via the filter, the target cells from the non-target cells and capturing the target cells;
a second step of placing the target cells, which have been captured by the filter, in a buffer solution;
a third step of causing the target cells that are within the buffer solution to cling to the glass slide, and adhering and transferring the target cells onto the glass slide while still living; and
a fourth step of immersing the glass slide in a container in which a preservation liquid is stored, and preserving the target cells that have been transferred onto the glass slide,
wherein a groove of a width of 1 to 5 µm and a depth of 1 to 5 µm is provided in the surface of the glass slide, and the groove is a drainage opening.

3. A method of preparing a glass slide specimen of cells with a filter unit that has a filter that has recesses, which capture target cells that are at least one of circulating tumor cells within blood or rare tumor cells within a body fluid, and pores that are formed in the recesses and that pass non-target cells therethrough, and that supplies blood or a body fluid to a surface at a target cell capturing side of the filter, the method comprising:
a first step of separating, via the filter, the target cells from the non-target cells and capturing the target cells;
a second step of superposing the glass slide on the filter, at a side at which the target cells are captured, placing a plate-like cover member on the filter, at a side opposite to the glass slide, and immersing the target cells, which are settled between the recesses of the filter and the glass slide, in a buffer solution;
a third step of transferring the target cells, which are between the filter and the glass slide, onto the glass slide under application of centrifugal force; and
a fourth step of, by immersing the glass slide to which the target cells are transferred, the cover member and the filter in a container in which a preservation liquid is stored, causing the cover member and the filter to peel-off naturally from the glass slide and preserving the target cells that have been transferred onto the glass slide, without impairing the target cells.

4. A method of preparing a glass slide specimen of cells with a filter unit that has a filter that has recesses, which capture target cells that are at least one of circulating tumor cells within blood or rare tumor cells within a body fluid, and pores that are formed in the recesses and that pass non-target cells therethrough, and that supplies blood or a body fluid to a surface at a target cell capturing side of the filter, the method comprising:
a first step of separating, via the filter, the target cells from the non-target cells and capturing the target cells;
a second step of gently putting the glass slide on the filter, at a side at which the target cells are captured, and immersing the target cells, which are settled between the recesses of the filter and the glass slide, in a buffer solution;
a third step of transferring the target cells, which are between the filter and the glass slide, onto the glass slide by a slow liquid flow of the buffer solution that is made under pressurization by air pressure; and
a fourth step of, by immersing the glass slide to which the target cells are transferred and the filter in a container in which a preservation liquid is stored, causing the filter to peel-off naturally from the glass slide and preserving the target cells that have been transferred onto the glass slide, without impairing the target cells, or by immersing the glass slide to which the target cells are transferred in the container, causing the target cells that have been transferred onto the glass slide to be preserved, without impairing the target cells.

* * * * *